(12) United States Patent
Merz et al.

(10) Patent No.: US 9,867,603 B2
(45) Date of Patent: Jan. 16, 2018

(54) RETRACTOR AND OPERATING METHOD

(71) Applicant: Karl Storz SE & Co. KG, Tuttlingen (DE)

(72) Inventors: Robin Merz, Furtwangen (DE); Jochen Stefan, Wald (DE); James Duncan Martin, Dundee (GB)

(73) Assignee: Karl Storz SE & Co. KG, Tuttlingen (DE)

( * ) Notice: Subject to any disclaimer, the term of this patent is extended or adjusted under 35 U.S.C. 154(b) by 97 days.

(21) Appl. No.: 14/618,473

(22) Filed: Feb. 10, 2015

(65) Prior Publication Data
US 2015/0223797 A1 Aug. 13, 2015

(30) Foreign Application Priority Data
Feb. 10, 2014 (DE) .................. 10 2014 101 602

(51) Int. Cl.
*A61B 1/32* (2006.01)
*A61B 17/02* (2006.01)

(52) U.S. Cl.
CPC ................ *A61B 17/0218* (2013.01)

(58) Field of Classification Search
CPC ........ A61B 17/02; A61B 17/0218; A61B 1/32
See application file for complete search history.

(56) References Cited

U.S. PATENT DOCUMENTS

| | | | | |
|---|---|---|---|---|
| 5,656,012 A * | 8/1997 | Sienkiewicz | ...... | A61B 17/0218 600/204 |
| 5,662,676 A * | 9/1997 | Koninckx | .......... | A61B 17/0218 606/198 |
| 5,752,961 A * | 5/1998 | Hill | ....................... | A61B 17/221 606/113 |
| 6,443,959 B1 * | 9/2002 | Beland | ................. | A61B 17/221 606/127 |

(Continued)

FOREIGN PATENT DOCUMENTS

| | | |
|---|---|---|
| DE | 19840880 A1 | 3/2000 |
| DE | 19920869 A1 | 12/2000 |

(Continued)

OTHER PUBLICATIONS

European Search Report Application No. EP 15 15 3600 Completed: Jun. 24, 2015; dated Jul. 3, 2015 4 pages.

*Primary Examiner* — Ellen C Hammond
*Assistant Examiner* — Tessa Matthews
(74) *Attorney, Agent, or Firm* — Whitmyer IP Group LLC

(57) ABSTRACT

A retractor for endoscopic surgery, having a first shaft portion, in which an actuation device is movable, and a second shaft portion coupled pivotably thereon. A transmission arm is articulated on a distal end of the actuation device. A retraction structure is connected to a distal end of the second shaft portion, which retraction structure can be releasably coupled, with its other end, to the second shaft portion via a coupling device. The coupling device has a slide, which is guided in the second shaft portion. The (Continued)

transmission arm is articulated on the second shaft portion by way of a peg-and-slot connection and is operatively coupled to the slide in order to move the latter longitudinally, wherein the coupling device can be transferred to a release state by longitudinal movement of the slide. An operating method for the retractor is also disclosed.

16 Claims, 4 Drawing Sheets

(56) References Cited

U.S. PATENT DOCUMENTS

| | | | | |
|---|---|---|---|---|
| 8,444,657 B2* | 5/2013 | Saadat | ............... | A61B 17/0401 606/139 |
| 8,562,593 B2* | 10/2013 | Bao | ............... | A61B 8/0841 606/1 |
| 8,821,518 B2* | 9/2014 | Saliman | ............. | A61B 17/0469 606/144 |
| 8,858,588 B2* | 10/2014 | Sigmon, Jr. | ............ | A61B 17/08 606/205 |
| 2003/0065337 A1* | 4/2003 | Topper | ............... | A61B 17/0469 606/144 |
| 2003/0176883 A1* | 9/2003 | Sauer | ................. | A61B 17/0218 606/198 |
| 2008/0058833 A1* | 3/2008 | Rizvi | ................. | A61B 17/4241 606/119 |
| 2010/0130817 A1* | 5/2010 | Conlon | .............. | A61B 17/0218 600/106 |

FOREIGN PATENT DOCUMENTS

| | | |
|---|---|---|
| EP | 0705566 A1 | 4/1996 |
| JP | 2013085772 A | 5/2013 |
| WO | 0067642 A2 | 11/2000 |

* cited by examiner

RETRACTOR AND OPERATING METHOD

FIELD OF THE INVENTION

The following invention relates to a retractor and to an operating method for the retractor.

BACKGROUND OF THE INVENTION

In endoscopic surgery, retractors are used to keep organs away from the operating site, so as to have a clear view and sufficient freedom of movement. The retractors usually have an actuation handle, which is coupled via a shaft to a flexible retraction structure, the latter being composed of several link elements that are interconnected in an articulated manner. For insertion into the body or for passage through a trocar, the link elements are oriented in alignment with the shaft, and it is only when inside the body that they are shaped to form a ring or hook for receiving the organ. In order to be closed to form a ring, the retraction structure has, on the last distal link element, a connecting means connected to the shaft. The ring is shaped with the aid of a second endoscopic instrument, for example gripping forceps, introduced through a further body opening, or by means of a Bowden wire, which is guided in the link elements themselves and which is actuated with the actuation handle. The hinges that connect the individual link elements are designed to be as nontraumatic as possible and can have guide surfaces and/or angled abutments that bring the individual hinges in each case to an optimal angle for closing the ring.

A retractor of the type in question is known from DE 199 20 869 A1 and has a shaft at whose distal end several articulated link elements are arranged that can be adjusted to form a ring, wherein a distal link element can be coupled to the shaft via two locking hooks. The link elements can be brought to the ring position with the aid of a Bowden wire, which is guided within the link elements. The retraction structure can be angled by up to 90° relative to the shaft by a hinge.

In addition to the locking hooks disclosed there, it is also known to arrange a locking pin at the free end of the retraction structure, which locking pin can be brought into releasable engagement with a spring pressure piece in the shaft. Considerable force has to be applied here, both for coupling and also for uncoupling, since the restoring force of the spring pressure piece always has to be overcome; this poses a high risk of injury since an operator can always slip when applying pressure. Moreover, the spring pressure piece can only be cleaned and disinfected with great effort. Proceeding from this prior art, the object of the present invention is to make available an improved retractor for endoscopic surgery, which retractor can be operated more reliably and with application of less force, is easier to clean, and has a high degree of safety as regards operating errors.

SUMMARY OF THE INVENTION

This object is achieved by a retractor and control method for endoscopic surgery according to the invention.

There is the further object of making available an operating method for such a retractor, which allows the retractor to be used more efficiently and in a way that saves time.

Preferred illustrative embodiments of the device and of the method are described by the dependent claims.

In a first embodiment, the retractor according to the invention for endoscopic surgery has a first shaft portion, within which an actuation device is guided movably, and which is pivotably coupled to a second shaft portion. Moreover, the retractor has a transmission arm, which at one end is articulated on a distal end of the actuation device and at its other end is articulated, eccentrically with respect to a rotation axis of the shaft portions, on the second shaft portion. One end of a retraction structure is connected to the distal end of the second shaft portion, and the other end of the retraction structure has a coupling end. With its coupling end, the retraction structure can be releasably coupled to a coupling device of the second shaft portion.

The coupling device has a slide, which is guided movably within the second shaft portion. The transmission arm is articulated on the second shaft portion by means of a peg-and-slot connection, wherein a slot of the peg-and-slot connection extends parallel to the longitudinal axis of the shaft portions when the shaft portions are extended. The transmission arm is operatively coupled to the slide in order to move the latter longitudinally, wherein the coupling device can be converted to a release state by the longitudinal travel of the slide.

The slide serves as part of a lock, which is opened for the assembly. Here, the tip or the distal or also "free" part of the ring of link elements can be guided through. If the slide is then moved axially, an undercut is generated which locks the tip of the ring of link elements in a fixed position secure against being pulled out.

Here, "within" signifies that the actuation device is guided in the first shaft portion and the slide is guided in the second shaft portion along the longitudinal axis.

The actuation device can be a mechanical actuation device, for example an actuation rod, an actuation cable or an actuation wire, or a combination of the aforementioned. However, the actuation device can also be a hydraulically actuatable device with an actuation piston that can be driven again along the longitudinal axis to the first shaft portion.

In the simplest case, the operative coupling of the transmission arm to the slide can be realized if the distal end of the transmission arm contacts the slide during a movement in the distal direction along the slot of the peg-and-slot connection, and, in this way, the movement is transmitted to the slide.

Retraction structures per se are known and are composed of several link elements, usually more than five, that are interconnected with at least one degree of freedom of movement via hinges.

In contrast to retractors according to the prior art, the coupling device of the retractor according to the invention is locked and released by active participation of the operator, wherein, in order to couple the coupling end of the retraction structure to the coupling device, no locking forces, such as a spring force, have to be overcome; when the coupling device is brought to its release state, the coupling end of the retraction structure can be coupled thereto without any great application of force. In this way, when coupling or uncoupling the coupling device, there is no longer any danger of slipping; even under confined spatial conditions in an operating field, the coupling end of the retraction structure can therefore be safely coupled to the second shaft portion in order to form the ring.

In a further embodiment of the retractor according to the invention, the slide can have a through-opening for the coupling end of the retraction structure. In a release state of the coupling device, the through-opening of the slide lies over an insertion opening which is provided in a wall of the second shaft portion for the coupling end of the retraction structure. A second slot extends from the through-opening in the distal direction and, in a locked state of the coupling device, at least partially overlaps the insertion opening in the wall of the second shaft portion. The dimensions of that portion of the coupling end of the retraction structure that is to be received correspond to the dimensions of the slot.

By means of the longitudinal axial movement of the slide, a "passage" for the coupling end of the retraction structure is thus created in the release state of the coupling device, whereas, in the locked state of the coupling device, the coupling end is held with a form fit by the interaction of the insertion opening and of the second slot of the slide. In particular, it is necessary to match the radial position of the coupling end of the retraction structure with respect to the second shaft portion, the width of the slot with respect to a diameter of the coupling end, and the thickness of the slide to a thickness of the coupling end. The through-opening and the second slot adjacent to it are not separate from each other but connected, such that an opening in the shape of a cylinder lock is obtained. This opening, which is movable relative to the insertion opening, cooperates with the insertion opening in order to provide the releasability of the coupling device.

In a further embodiment, the coupling end of the retraction structure can comprise a securing pin, which can preferably have a throat. The dimensions of the throat correspond to the slot of the slide. Advantageously, the securing pin can also have a mushroom-shaped head; a spherical head may also be used but is not as good as a mushroom head, since this possibly has more play in the "lock".

A securing pin with a spherical head can be brought into engagement with the coupling device much more easily than a securing pin with a flat head, since it more or less finds its own way into the coupling device. In the same way as in a ball joint, a securing pin with a spherical head also permits angle mobility within certain limits, which is advantageous in particular for avoiding injury to the held tissue or to the surrounding tissue.

According to a further embodiment, the slot of the peg-and-slot connection can be present in a distal end portion of the transmission arm. This slot can be engaged with a peg which for its part is arranged in a fixed position in a proximal end portion of the second shaft portion.

From the point of view of manufacturing technology, the slot of the peg-and-slot connection can be produced much more easily in the transmission arm than in the second shaft portion. Functionally, however, it is also possible that the slot lies in the second shaft portion and the peg is connected fixedly to the transmission arm.

From the point of view of manufacturing technology, it would also be possible to produce the slot in the second shaft portion, in which case the slot does not necessarily have to be made on the inside. Here, a non-continuous contour would be conceivable (more or less like a blind hole), or also a continuous one in the sense of a through-bore. The connection could then be realized with a pin, for which purpose a corresponding bore would have to be made in the transmission arm. From the point of view of manufacturing technology, it is easier to work on a plane surface, such as that of the transmission arm, than on a curved surface, such as that of a cylinder.

Functionally, however, it would be conceivable for bore and slot to be equivalent and interchangeable.

Furthermore, the slide can have, at a proximal end, a channel which extends perpendicularly with respect to a pivot plane of the shaft portions. The distal end of the transmission arm is received in the channel, wherein an outer contour of the cross section of the distal end of the transmission arm corresponds to a contour of the cross section of the channel.

Here, "cross section" is to be understood with reference to the orientation of the channel and not with reference to the longitudinal axis of the shaft or of the shaft portions. By interaction of the channel with the distal end of the transmission arm, a form-fit coupling of the transmission arm to the slide can be achieved. By way of this form-fit coupling, the slide can be moved both in the distal direction and also in the proximal direction, since the transmission arm is moved indirectly by the actuation device. The coupling device can be triggered by distal movement of the slide, and the slide can also be driven back to its locked position. A return device, for example a spring, is not necessary for the return of the slide; the slide is positively coupled to the transmission arm. Moreover, the movement of the transmission arm in a distal direction is blocked by the positive coupling of the distal end to the channel of the slide, when the two shaft portions are pivoted at an angle to each other; it is released only when the shaft portions are extended. This prevents accidental opening of the coupling device by the action of an external force.

According to a further embodiment, the channel can have a circular cross section, wherein the center point of the circular cross section preferably lies in an axis with the peg of the peg-and-slot connection. Since the center point of the channel and the axis of the peg are the same, the longitudinal axial position of the slide remains unchanged during a rotation of the second shaft portion. The "lock", as has been explained above, thus always remains closed in an angled position. If the centers of rotation were not identical, this would mean that, during a pivoting of the second shaft portion, the slide would be forced to move and the lock would open or even close further, which can lead to wear on the instrument or, in the worst case, to release of the lock.

In addition, the second shaft portion and the transmission arm can be positively coupled via a slotted guide. In particular, the transmission arm can have, adjacent to the slot, a guide groove which extends along a proximal groove portion parallel to the slot and extends along a distal groove portion parallel to the cross-sectional contour of the channel. A guide pin is guided movably in the guide groove and is arranged in a fixed position on the second shaft portion. Here too, the components cooperating with each other can be interchangeable as equivalents: the groove can be present on the slide instead of on the transmission arm, which guides the slide.

The stated directions of the guide groove are each in relation to the extended state of the shaft portions. By means of the additional positive coupling, it is possible to considerably reduce a mutual play of the two shaft portions, which otherwise occurs particularly at small pivot angles. In particular, the two shaft portions can be coupled with little play even when the manufacturing tolerances are quite high. If the retractor does not have the additional positive guidance, this means that, if a radial force acts on the second shaft portion in the pivoting direction, play occurs that corresponds to the play of the peg in the slot of the peg-and-slot connection.

Furthermore, in order to achieve an appealing design, the guide groove of the slotted guide can be closed at least at its distal end, as a result of which an angle limitation can additionally be achieved, which itself takes place via the hinge. The guide groove can, for example, extend so far in the distal direction that an angle limitation takes place only at a pivot angle of 90° or else at a smaller angle.

Furthermore, a resetting device for the slide can be arranged between the second shaft portion and the slide, which resetting device can, in particular, be a spring. The resetting device is provided, particularly in an embodiment without form-fit coupling of the transmission arm to the slide, in order to guide the slide back in the longitudinal axial direction to a position corresponding to the locked state of the coupling device.

Moreover, the second shaft portion can be articulated on the first shaft portion via a hinge, wherein the hinge preferably has a body which is connected to one of the shaft portions. Adjacent to a rotation axis of the hinge, the body of the hinge can have a guide track along a circumferential portion. A pin of the respective other shaft portion is guided in the guide track.

The guide track is, in particular, a guide track that is closed at both ends and that is provided for additional angle limitation at both end positions. Here, in the circumferential direction means that the guide track runs at a constant distance from the rotation axis of the hinge, i.e. in the shape of an arc of a circle.

The body of the hinge can moreover have a cylindrical receiving portion, which is preferably received in a receiving bore, for example a blind hole, of one shaft portion. The receiving bore can extend from an end face of the respective shaft portion directed toward the respective other shaft portion. However, provision can also be made that the hinge is a "double hinge" with two hinge bodies which are each secured on another shaft portion and in which a respective pin is guided. As the hinge body is designed as a separate component, the overall retractor can be more easily produced, because the manufacturing tolerances chosen for the production of the first and second shaft portion can be relatively wide, since active surfaces do not have to be machined, or active surfaces are assigned to the separate component.

Finally, a handle can be connected to a proximal end of the first shaft portion and has one or more actuation elements. At least one actuation element is operatively coupled to the actuation device and is designed to move the actuation device in a predetermined range of travel.

The actuation element can be, for example, a rotary wheel, a lever, a slide, a forceps grip and/or a pistol trigger. Actuation elements are known and are used in different designs in endoscopic and/or laparoscopic instruments. The length of the first shaft portion can be from about 10 cm to over 60 cm in order to reach an operating site within a human or animal body. The predetermined range of travel here includes the travel that the actuation device needs to cover in the distal direction in order to transfer the coupling device to the release state. A person operating the retractor has to take care not to move the actuation element too far in the distal direction, so as not to accidentally trigger the release of the coupling device.

In order to prevent this, an additional distal range of travel of the actuation element of the handle can be freed, which additional range of travel is at least as long as a travel of the slide between its release state and its locked state. It is thus possible to ensure that the operator cannot accidentally bring about the release of the coupling device and instead, by acting on the handle, first of all has to free the additional range of travel provided for the triggering. Here, "range of travel" is to be understood in relation to the longitudinal axial movement of the actuation device and not in relation to a movement of the actuation element, since a certain transmission ratio will always be provided between a movement or rotation of the actuation element and the translatory movement of the actuation device.

The operating method according to the invention for the retractor has, in a first embodiment, the following steps:

a) bringing the first shaft portion and second shaft portion to an extended position, b) moving the actuation device in the distal direction as far as a predetermined end position, thereby moving the transmission arm along the slot of the peg-and-slot connection and entraining the slide, thereby obtaining the release state of the coupling device, c) guiding the coupling end of the retraction structure to the coupling device of the second shaft portion and connecting it to the coupling device, d) moving the actuation device in the proximal direction, thereby entraining the slide and transferring the coupling device to the locked state, and locking the coupling end of the retraction structure in the coupling device.

For release, the coupling end of the retraction structure is pulled out instead.

Moreover, step d) can be followed by step e), i.e. further moving the actuation device in the proximal direction, thereby entraining the transmission arm in the proximal direction and bringing a distal wall of the slot of the transmission arm into contact with the peg and transferring the movement of the actuation device to the second shaft portion, thereby obtaining a pivoting movement of the second shaft portion.

In contrast to known retractors in which the coupling end of the retraction structure is coupled to the second shaft portion by a spring compression piece, the insertion of the coupling end is quicker and easier by the methods according to the invention and using the retractor according to the invention, since no locking force has to be overcome. During the coupling procedure, the operator has less risk of seeing a forceps or the like slip off the retraction structure, as a result of which the coupling of the retraction structure can take place more quickly and after just a few failed attempts, as a result of which the entire operation is made more efficient.

In a further embodiment, in step c) the actuation device can be moved in the distal direction until the through-opening of the slide and the insertion opening of the second shaft portion lie one over the other. In addition, in step d), the securing pin of the retraction structure is fitted into the insertion opening of the second shaft portion and through the through-opening of the slide, and in step e), the actuation device is moved in the proximal direction until the insertion opening of the second shaft portion at least partially overlaps the slot of the slide.

Furthermore, the actuation device can be moved by means of the actuation element of the handle. Step b) is preferably preceded by step a'), i.e. freeing the additional range of travel of the actuation element of the handle.

These and further advantages are set forth in the following description with reference to the attached figures. The reference made in the description to the figures is for assisting with the description and for simplified understanding of the subject matter. Items or parts of items that are substantially equal or similar can be provided with the same reference signs. The figures are merely schematic depictions of illustrative embodiments of the invention.

DETAILED DESCRIPTION OF THE INVENTION

Figure 1:
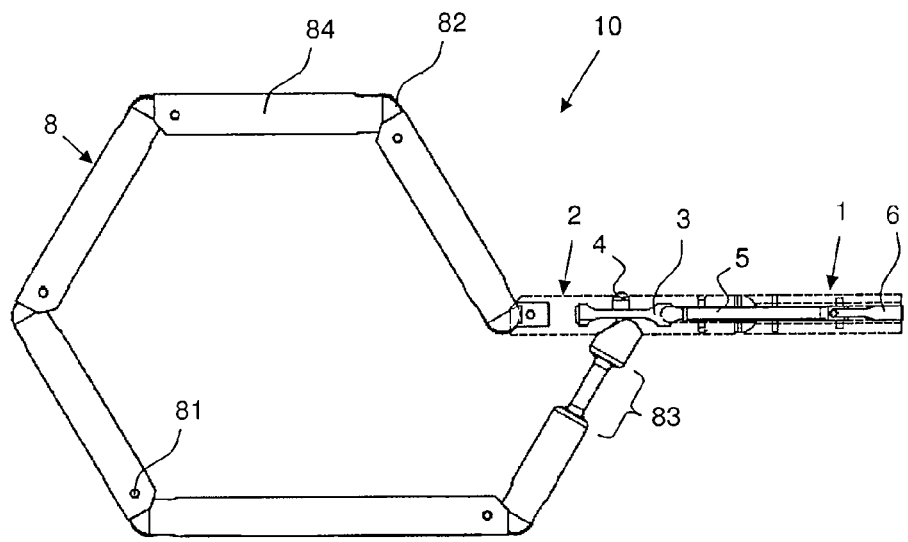
FIG. 1 shows a plan view of a distal part of the retractor.

FIG. 1 shows the retractor 10 according to the invention, composed mainly of the retraction structure 8 and also of the first shaft portion 1 and second shaft portion 2. The retraction structure 8 is provided for the purpose of being placed under or around an organ, for example under the liver, in order to hold the latter away from an operating site, wherein the retraction structure 8 is in most cases positioned under an organ in order to avoid "blind" maneuvering behind the organ. The retraction structure 8 has several ring elements 84, which are connected to each other via hinges so as to be pivotable about the hinge axes. The visible fixing pin 81 is responsible for fixing the ball joint, while the hinge axle is concealed. The hinges each have a nontraumatic, rounded hinge body 82, such that no tissue parts can get caught therein. At its free end, the retraction structure 8 is connected to the distal end of the second shaft portion 2, and its other end is likewise connected to the latter, substantially transversely with respect to the second shaft portion 2. The connection of the free end of the retraction structure 8 to the second shaft portion 2 is releasable and, in an operation, it is closed only at the operating site, so as to keep the size of the access route/incision to the operating field as small as possible.

The free end moreover has an engagement area 83 for an additional tool for assembly or disassembly of the retraction structure 8, which engagement area 83 is designed such that it can be gripped comfortably and in a manner secure against slipping.

At its "free end" or coupling end, the retraction structure 8 comprises a securing pin 4, which engages with a form fit in a coupling device of the second shaft portion 2, wherein the coupling device can be released by a slide 3; for this purpose the slide 3 is moved in the distal direction by means of the actuation device 6 and the transmission arm 5 in the extended position, as a result of which the form-fit engagement of the securing pin 4 in the coupling device is canceled. When removing the securing pin 4 from the coupling device, it is advantageous that no locking force, of the kind generated in known retractors by a spring pressure piece for example, has to be overcome; instead, the securing pin 4 can be uncoupled freely and without applying force.

The first shaft portion 1 and the second shaft portion 2 are pivotably connected, the pivot plane being perpendicular to the image plane of FIG. 1, such that the second shaft portion 2 can be pivoted out from the image plane. For this purpose, an actuation rod 6 is guided so as to be movable along the longitudinal axis in the first shaft portion 1, the distal end of said actuation rod 6 being articulated on a transmission arm 5 (see FIG. 2), which in turn is articulated on the second shaft portion 2 for generating the pivoting movement.

The retractor 10 according to the invention can be actuated by means of a conventional handle, as is known in the form of forceps, pistol, ring and scissor grips, wherein the handle is coupled to the first shaft portion 1 at a proximal end of the first shaft portion 1, which lies in an area to the right of and outside of the area shown in the figure and with which the actuation rod 6 can be actuated. It is suitable to use a handle that allows a proximal "over-open position" to be obtained, as a result of which the "lock", formed by the slide 3 and the insertion opening 27 of the second shaft portion 2, can be actuated.

Figure 2:
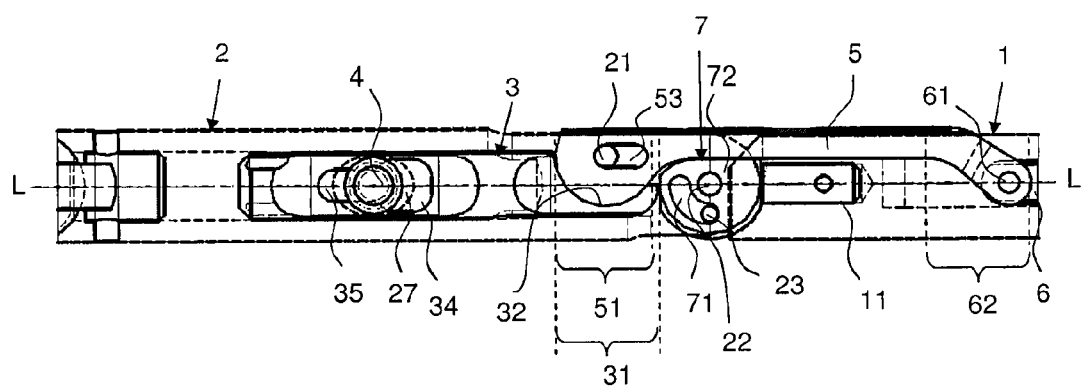
FIG. 2 shows a partial sectional view of the shaft portions in the extended state.

FIG. 2 shows a partial view that better illustrates the mechanical conversion for release of the coupling device and for pivoting the second shaft portion 1, wherein the first shaft portion 1 and the second shaft portion 2 are shown in section along the longitudinal axis. The second shaft portion 2 is mounted rotatably about the peg 22 via a hinge 7, of which the hinge body 72 is received in a blind hole 11 of the first shaft portion 1.

The transmission arm 5 is articulated on the actuation rod 6, in the distal end portion 62 thereof, by means of a connecting pin 61 and extends as far as a proximal end portion of the second shaft portion 2, where it is articulated on the second shaft portion 2 in a manner eccentric to the longitudinal axis L and eccentric to the rotation axis of the two shaft portions 1, 2. A pulling movement of the actuation rod 6 thus effects a rotation movement of the second shaft portion 2 about the peg 22. The articulation of the second shaft portion 2 on the first shaft portion 1 is realized by means of a hinge 7, which has a hinge body 72. To limit the range of pivoting of the second shaft portion 2, a guide track 71 is present in the hinge body 72, which guide track 71 is designed extending along an arc of a circle about the peg 22, and in which the rotation angle limitation pin 23 is guided.

In FIG. 2, only the securing pin 4 of the retraction structure 8 is shown, while the ring elements 84 themselves are cut away. The coupling device for the securing pin 4 is formed by the interaction of the slide 3 with the wall of the second shaft portion 2. The slide 3 has a through-opening 34 for the securing pin 4, which through-opening 34 is adjoined distally by a second slot 35 whose width is smaller than the diameter of the through-opening 34. The securing pin 4 has in particular a circumferential throat (see FIG. 7), of which the diameter, height and position are adapted to the slot 35 of the slide 3. The second shaft portion 2 has an insertion opening 27 for the securing pin 4, which insertion opening 27 is present in opposite portions of the wall of the second shaft portion 2 and through which the securing pin 4 can be fitted as soon as the slide has traveled in the distal direction and the through-opening 34 lies over the insertion opening 27. For locking purposes, the slide 3 is moved in the proximal direction until the slot 35 overlaps the insertion opening 27 and is in engagement with the throat (see FIG. 7) of the securing pin 4. However, the coupling device can be actuated only in the extended state of the shaft portions 1, 2, whereas no actuation is possible in the case of substantial pivoting, as a result of the force direction of the actuation rod 6.

For force transmission, the slide 3 has, at its proximal end 31, a channel 32 which has a circular cross section and in which the distal end 51 of the transmission arm 5 is received. The cross sections of the distal end of the transmission arm 5 and of the channel 32 of the slide 3 correspond both in terms of their shape and also their dimensions, as a result of which a positive coupling with little play is obtained, and both tensile forces and also pressure forces can be transmitted from the transmission arm 5 to the slide 3. The direction and distance along which the transmission arm is movable is predefined by the slot 53 present in the distal end portion 51 of the transmission arm 5.

Figure 3:
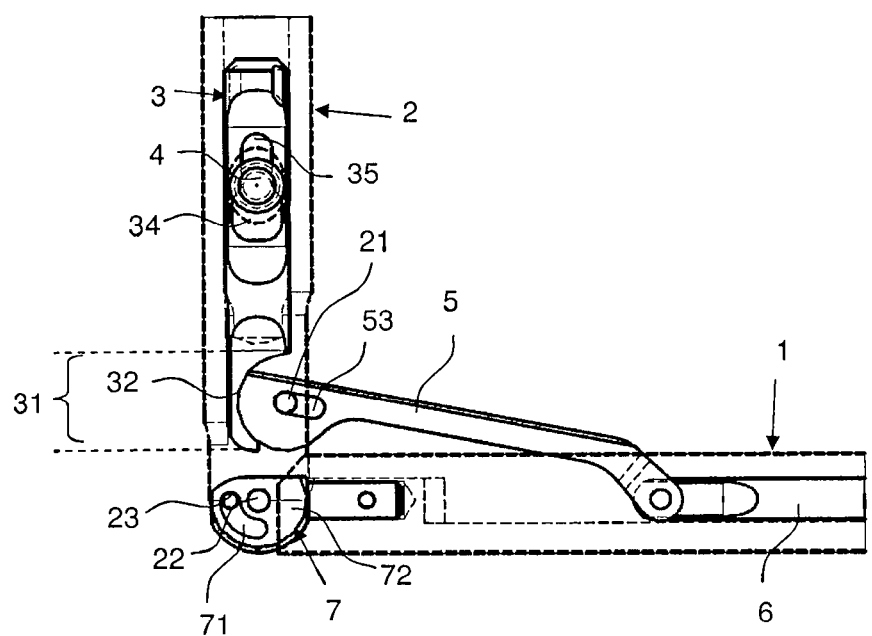
FIG. 3 shows a partial sectional view of the shaft portions in the angled state.

FIG. 3 shows the two shaft portions 1, 2 in an angled state. Starting from this position, the second shaft portion 2 cannot be pivoted out any further, since the rotation angle limitation pin 23, which is guided in the guide track 71 of the hinge body 72, abuts the end of the guide track 71.

However, when an external radial force acts on the second shaft portion 2, play occurs in the mechanism, in particular about the rotation axis 22, the maximum extent of which play corresponds to the length of the slot 53. The play is caused especially by manufacturing tolerances in the guiding of the rounded distal end of the transmission arm 5 in the channel 32 and a radial play of the slide 3 in its longitudinal axial guide in the second shaft portion 2. In addition to the stated operative connections with tolerances, it is also possible for further manufacturing tolerances, for example in the rotation axis 22 or in the articulation of the transmission arm 5 on the actuation element 6, to lead to increased play about the rotation axis 22.

Elastic bending also occurs, particularly when the shaft portions 1, 2 are made of plastic. Since the guide track 71 and the pin 23 lie very close to the rotation axis of the two shaft portions 1, 2, very considerable locking forces occur there, which, when the second shaft portion is subjected to a radial force, can cause an elastic bending of the second shaft portion, as a result of which the peg 21 will also move in the slot 53. When the shaft portions 1, 2 are made of steel, however, the elastic bending under the typical loads will be small. However, should play occur, there is no danger of the slide 3 being moved and of the coupling device thus accidentally being transferred to the release state.

Figure 4:
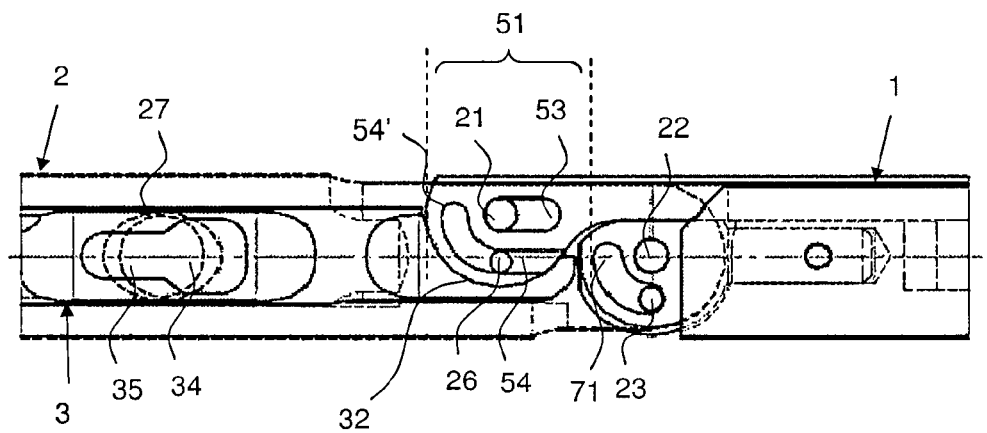
FIG. 4 shows a side view of a part of the shaft portions with transparent second shaft portion and the slide in the locked state.
Figure 5:
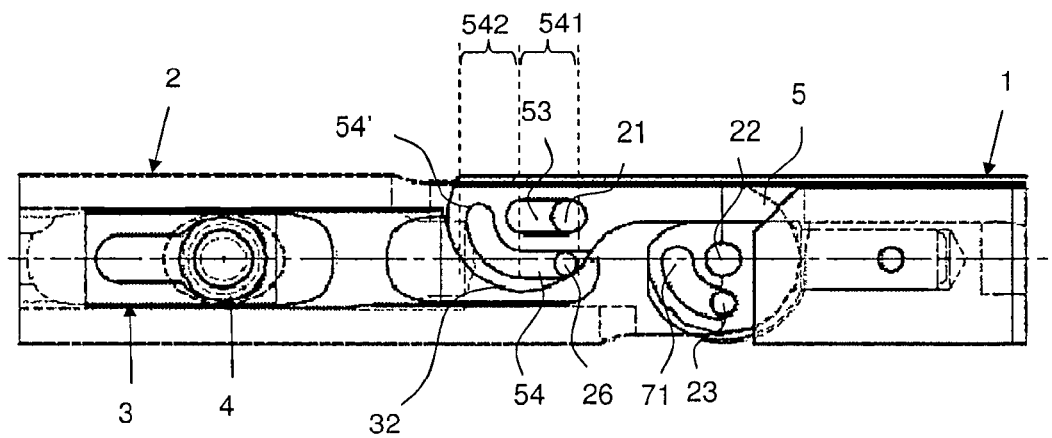
FIG. 5 shows a side view of a part of the shaft portions with transparent second shaft portion and the slide in the release state.
Figure 6:
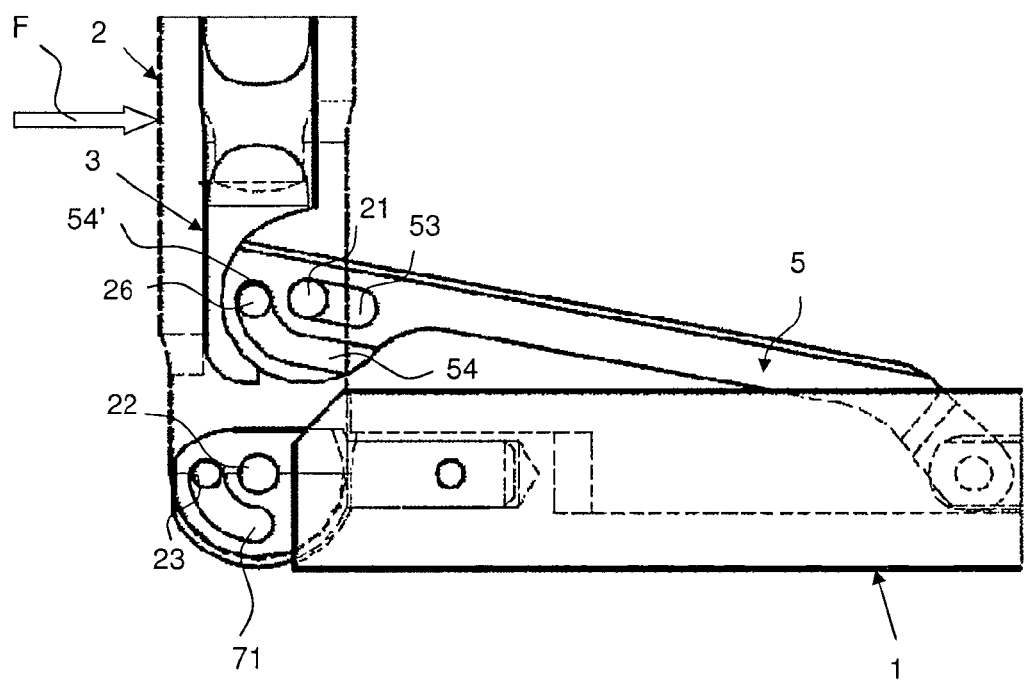
FIG. 6 shows a side view of a part of the shaft portions in the angled state with transparent second shaft portion.

In order to reduce the play in the articulation of the two shaft portions 1, 2, the measure shown in FIG. 4 to FIG. 6 is proposed according to the invention.

Adjacent to the slot 53, a guide groove 54 is present in the distal end portion of the transmission arm 5. The guide groove 54 has a proximal groove portion 541, in which it extends parallel to the slot 53, and a distal groove portion 542, in which it follows the cross-sectional contour of the channel 32. The proximal groove portion 541 allows the slide 3 to be moved furthermore along the slot 53 to release the coupling device, while the distal groove portion 542 is intended to prevent play occurring when an external radial force acts on the second shaft portion 2. Further embodiments are also possible in which, however, the guide groove 54 sits on the slide 3.

The coupling device is shown in the locked state in FIG. 4; the slide 3 is moved in the proximal direction and the peg 21 bears on its distal abutment. The insertion opening 27 of the second shaft portion 2 is blocked by the slot 35 in the slide. By contrast, FIG. 5 shows the release state of the coupling device; the slide 3 is moved fully in the distal direction and the peg 21 bears on its proximal abutment. In this state, the securing pin 4 can be fitted into the insertion opening 27 and through the through-opening of the slide 3, since the through-opening 34 lies exactly over the insertion opening 27.

FIG. 6 shows an angled position. The closed end 54' of the guide groove 54 provides a merely additional angle limitation by way of its closed end 54'. Moreover, by using the slotted guide formed by the guide groove 54 and the guide pin 26, slight play occurs when an external radial force acts on the second shaft portion 2. In the case of a load applied in the direction shown by the arrow F, the second shaft portion 2, without the slotted guide, would be able to pivot according to a total play composed of said components. The slotted guide prevents this, since the curved distal groove portion 542 (see FIG. 5) is almost at right angles to the force direction F; the pivoting of the second shaft portion 2 is blocked with a form fit or reduced to an amount corresponding to the transverse play of the guide pin 26 in the guide groove 54.

Figure 7:
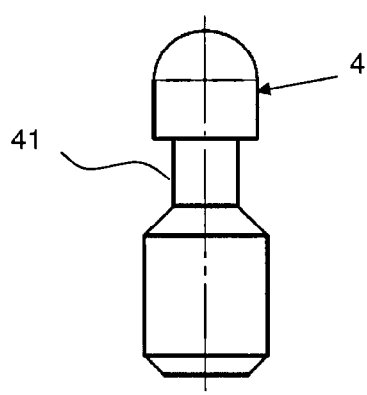
FIG. 7 shows a securing pin in a perspective view.

FIG. 7 shows the securing pin 4, which is intended to be arranged with its plane end face on the distal end of a retraction structure 8 (see FIG. 1). It has a mushroom-shaped head, which is designed for engagement with the slot of the slide 3 (see FIG. 2 to FIG. 6).

LIST OF REFERENCE SIGNS

1 first shaft portion
10 distal part of the retractor
11 blind hole of the first shaft portion
2 second shaft portion
21 peg of the second shaft portion
22 peg/rotation axis
23 pin/rotation angle limitation pin
26 guide pin of the slotted guide
27 insertion opening of the second shaft portion
3 slide
31 proximal end portion of the slide
32 channel of the slide
34 through-opening
35 second slot, slot of the slide
4 securing pin
41 throat
5 transmission arm
51 distal end portion of the transmission arm
53 slot of the transmission arm
54 guide groove of the slotted guide
54' distal end of the guide groove
541 proximal groove portion
542 distal groove portion
6 actuation rod
61 connecting pin
62 distal end portion of the actuation rod
7 hinge of the stationary shaft portion
71 guide track of the hinge
72 hinge body
8 retraction structure
81 fixing pin of a ball joint
82 hinge body
83 engagement area for the additional tool for disassembly/assembly
84 link element of the retraction structure

The invention claimed is:

1. A retractor for endoscopic surgery, comprising
a first shaft portion, within which an actuation device is guided movably, and which is pivotably coupled to a second shaft portion, and
a transmission arm, which at one end is articulated on a distal end of the actuation device and at the other end is articulated, eccentrically with respect to a rotation axis of the shaft portions, on the second shaft portion, and
a retraction structure, which at one end is connected to a distal end of the second shaft portion and at the other end has a coupling end with which it can be releasably coupled to the second shaft portion via a coupling device, characterized in that the coupling device has a slide, which is movably guided within the second shaft portion, and the transmission arm is articulated on the second shaft portion by a peg-and-slot connection, wherein a slot of the peg-and-slot connection extends parallel to a longitudinal axis when the shaft portions are extended, and wherein the transmission arm is operatively coupled to the slide in order to move the slide longitudinally, and wherein the longitudinal travel of the slide makes available a release state of the coupling device.

2. The retractor according to claim 1, characterized in that the slide has a through-opening for the coupling end of the retraction structure, in which the through-opening, in the release state of the coupling device, lies over an insertion opening in a wall of the second shaft portion for the coupling end of the retraction structure, and wherein a second slot extends from the through-opening in the distal direction and, in a locked state of the coupling device, at least partially overlaps the insertion opening, wherein dimensions of the second slot correspond to dimensions of a portion of the coupling end of the retraction structure that is to be received.

3. The retractor according to claim 2, characterized in that the coupling end of the retraction structure comprises a securing pin, which has a throat whose dimensions correspond to the slot of the slide, wherein the securing pin has a mushroom-shaped head.

4. The retractor according to claim 1, characterized in that the slot of the peg-and-slot connection is present on a distal end portion of the transmission arm and engages with a peg of the peg-and-slot connection which is arranged in a fixed position in a proximal end portion of the second shaft portion, or in that the slot of the peg-and-slot connection is present in a proximal end portion of the second shaft portion and engages with the peg of the peg-and-slot connection which is arranged in a fixed position on a distal end portion of the transmission arm.

5. The retractor according to claim 1, characterized in that the slide has, at a proximal end, a channel which extends perpendicularly with respect to a pivot plane of the shaft portions and in which a distal end of the transmission arm is received, wherein an outer contour of a cross section of the distal end of the transmission arm corresponds to a cross-sectional contour of the channel.

6. The retractor according to claim 5, characterized in that the channel has a circular cross section, wherein a center point of the circular cross section of the channel lies in an axis of the peg of the peg-and-slot connection.

7. The retractor according to claim 5, characterized in that the second shaft portion and the transmission arm are positively coupled via a slotted guide, wherein at least one guide groove is present on the distal end of the transmission arm, in which the at least one guide groove extends along a proximal groove portion parallel to the slot and extends along a distal groove portion parallel to the cross-sectional contour of the channel, wherein a guide pin is movably guided in the guide groove and is arranged in a fixed position on the the second shaft portion.

8. The retractor according to claim 1, characterized in that a resetting device for the slide is arranged between the second shaft portion and the slide.

9. The retractor according to claim 1, characterized in that the second shaft portion is articulated on the first shaft portion via a hinge, wherein the hinge has a body which is connected to one of the shaft portions and, adjacent to a rotation axis of the hinge, has a guide track extending along a circumferential portion, in which a pin of the respective other shaft portion is guided.

10. The retractor according to claim 9, characterized in that the body of the hinge has a cylindrical receiving portion, which is received in a receiving bore of the first shaft portion or of the second shaft portion, in which the bore extends from an end face directed toward the respective other shaft portion.

11. The retractor according to claim 1, characterized in that a handle is connected to a proximal end of the first shaft portion and has at least one actuation element which is operatively coupled to the actuation device and which is designed to move the actuation device in a predetermined range of travel.

12. The retractor according to claim 11, characterized in that an additional distal range of travel of the actuation element of the handle can be freed, which is at least as long as the longitudinal travel of the slide from the release state of the coupling device to a locked state of the coupling device.

13. An operating method for a retractor comprising the following steps:
 a) bringing a first shaft portion and a second shaft portion of the retractor to an extended position, the first shaft portion pivotably coupled to the second shaft portion, and the first shaft portion having an actuation device that is guided movably within,
 b) moving the actuation device in a distal direction as far as a predetermined end position, thereby moving a transmission arm along a slot of a peg-and-slot connection and entraining a slide, thereby obtaining a release state of a coupling device, wherein
  the slot of the peg-and-slot connection extends parallel to a longitudinal axis when the shaft portions are extended,
  one end of the transmission arm is articulated on a distal end of the actuation device, and at the other end is articulated eccentrically with respect to a rotation axis of the shaft portions, on the second shaft portion,
  the slide is part of the coupling device and is movably guided within the second shaft portion, and
  the transmission arm is operatively coupled to the slide in order to move the slide longitudinally, and a longitudinal travel of the slide makes available the release state of the coupling device,
 c) guiding a coupling end of a retraction structure to the coupling device of the second shaft portion and connecting it to the coupling device, the opposite end of the retraction structure being connected to a distal end of the second shaft portion,
 d) moving the actuation device in the proximal direction, thereby entraining the slide and transferring the coupling device to a locked state, and locking the coupling end of the retraction structure in the coupling device.

14. The operating method according to claim 13, wherein step d) is followed by step e), i.e. further moving the actuation device in the proximal direction, thereby entraining the transmission arm in the proximal direction and bringing a distal wall of the slot of the transmission arm into contact with the peg and transferring the movement of the actuation device to the second shaft portion, thereby obtaining a pivoting movement of the second shaft portion.

15. The operating method according to claim 13, wherein step b) involves moving the actuation device in the distal direction until the through-opening of the slide and the insertion opening of the second shaft portion lie one over the other, and step c) fitting the securing pin of the retraction structure into the insertion opening of the second shaft portion and through the through-opening of the slide, and step d) moving the actuation device in the proximal direction until the insertion opening of the second shaft portion at least partially overlaps the slot of the slide.

16. The operating method according to claim 13, wherein the actuation device is moved by the actuation element of the handle, and wherein step b) is preceded by step a'), i.e. freeing the additional range of travel of the actuation element of the handle.

* * * * *